US008821471B2

(12) United States Patent
Bianco et al.

(10) Patent No.: US 8,821,471 B2

(45) Date of Patent: Sep. 2, 2014

(54) DRUG BAG CONTAINER

(75) Inventors: Walter Bianco, Trieste (IT); Fabio Fioravanti, Trieste (IT)

(73) Assignee: Health Robotics S.r.l., Bolzano (IT)

( * ) Notice: Subject to any disclaimer, the term of this patent is extended or adjusted under 35 U.S.C. 154(b) by 0 days.

(21) Appl. No.: 13/476,138

(22) Filed: May 21, 2012

(65) Prior Publication Data

US 2012/0296308 A1 Nov. 22, 2012

(30) Foreign Application Priority Data

May 20, 2011 (IT) .............................. BO2011A0289

(51) Int. Cl.
*A61B 19/00* (2006.01)

(52) U.S. Cl.
USPC .......................................................... 604/408

(58) Field of Classification Search
USPC .......................................................... 604/408
See application file for complete search history.

(56) References Cited

U.S. PATENT DOCUMENTS 3,042,086 A * 7/1962 Winchell ...................... 141/390
3,079,919 A * 3/1963 Harrison et al. ............. 604/408
3,776,411 A 12/1973 Luckadoo
3,878,909 A * 4/1975 Treiber ......................... 177/145
4,561,110 A * 12/1985 Herbert ......................... 604/408
4,614,267 A * 9/1986 Larkin .......................... 206/221
4,711,359 A * 12/1987 White et al. ................. 215/11.1
4,759,756 A * 7/1988 Forman et al. ............... 604/413
4,762,248 A * 8/1988 Uhlig ............................ 206/508
4,821,895 A * 4/1989 Roskilly ....................... 215/11.1
4,906,103 A * 3/1990 Kao .............................. 366/130
5,084,041 A * 1/1992 Oxley et al. ................... 604/410
5,170,888 A * 12/1992 Goncalves .................... 206/222
5,207,509 A * 5/1993 Herbert .......................... 383/38
5,254,189 A * 10/1993 Hirobe et al. .................. 156/64
5,307,955 A * 5/1994 Viegas .......................... 222/107
5,383,906 A * 1/1995 Burchett et al. .............. 606/236
5,487,750 A * 1/1996 Burchett et al. .............. 606/236
5,520,166 A * 5/1996 Ritson et al. ............. 128/200.14
5,573,109 A * 11/1996 Isacson ........................ 206/38.1
5,728,086 A * 3/1998 Niedospial, Jr. .............. 604/408
5,789,684 A * 8/1998 Masek et al. ............... 73/864.91
5,824,012 A * 10/1998 Burchett et al. .............. 606/236
5,910,138 A * 6/1999 Sperko et al. ................. 604/408
6,200,295 B1 * 3/2001 Burchett et al. .............. 604/218
6,267,564 B1 * 7/2001 Rapheal ........................ 417/234
6,582,653 B1 * 6/2003 Warburton-Pitt ............... 422/26
6,786,330 B2 * 9/2004 Mollstam et al. ............. 206/222
7,092,797 B2 * 8/2006 Gaines et al. ................. 700/282

(Continued)

FOREIGN PATENT DOCUMENTS

EP 0686565 12/1995
EP 1086707 3/2001

OTHER PUBLICATIONS

Italian Search Report dated Feb. 17, 2012.

*Primary Examiner* — Susan Su
*Assistant Examiner* — Guy K Townsend
(74) *Attorney, Agent, or Firm* — McCarter & English, LLP

(57) ABSTRACT

A drug bag is housed inside a container, which has two shells movable between an open position and a closed position; and a gripper fitted outside the shells and defined by two jaws movable between a grip position and a release position to grip and release at least one conduit allowing access to the content of the bag.

7 Claims, 3 Drawing Sheets

(56) References Cited

U.S. PATENT DOCUMENTS

| | | | | |
|---|---|---|---|---|
| 7,175,614 | B2 * | 2/2007 | Gollier et al. | 604/410 |
| 7,354,426 | B2 * | 4/2008 | Young | 604/403 |
| 7,410,155 | B2 * | 8/2008 | Spain, III | 269/71 |
| 7,618,405 | B2 * | 11/2009 | Young | 604/403 |
| 7,621,411 | B2 * | 11/2009 | Doherty et al. | 215/228 |
| 7,658,721 | B2 * | 2/2010 | Steiner et al. | 604/24 |
| 7,867,204 | B2 * | 1/2011 | Bartholomew et al. | 604/249 |
| 7,876,204 | B2 * | 1/2011 | Taylor | 340/435 |
| 8,028,860 | B2 * | 10/2011 | Seelhofer | 222/107 |
| 8,302,803 | B1 * | 11/2012 | Greenberg et al. | 220/703 |
| 8,323,259 | B2 * | 12/2012 | Smith et al. | 604/415 |
| 2002/0190079 | A1 * | 12/2002 | Hamamoto | 222/105 |
| 2003/0000632 | A1 * | 1/2003 | Sperko et al. | 156/229 |
| 2003/0047467 | A1 * | 3/2003 | Smith et al. | 206/221 |
| 2003/0141268 | A1 * | 7/2003 | Kerns et al. | 215/11.1 |
| 2004/0068960 | A1 * | 4/2004 | Smith et al. | 53/396 |
| 2004/0129270 | A1 * | 7/2004 | Fishman | 128/204.18 |
| 2005/0077324 | A1 * | 4/2005 | Redmond | 222/541.9 |
| 2006/0042633 | A1 * | 3/2006 | Bishop et al. | 128/207.18 |
| 2006/0074348 | A1 * | 4/2006 | Spray et al. | 600/576 |
| 2006/0106345 | A1 * | 5/2006 | Flaker et al. | 604/131 |
| 2006/0113411 | A1 * | 6/2006 | Buckley | 241/100 |
| 2006/0272964 | A1 * | 12/2006 | Vogel et al. | 206/219 |
| 2007/0077655 | A1 * | 4/2007 | Unger et al. | 435/404 |
| 2007/0135766 | A1 * | 6/2007 | Fournie et al. | 604/131 |
| 2007/0149731 | A1 * | 6/2007 | Myers | 526/154 |
| 2007/0160506 | A1 * | 7/2007 | Ross et al. | 422/120 |
| 2007/0272705 | A1 * | 11/2007 | Beine et al. | 222/107 |
| 2008/0044603 | A1 * | 2/2008 | Hutchinson et al. | 428/35.7 |
| 2008/0047550 | A2 * | 2/2008 | Steiner et al. | 128/200.23 |
| 2008/0275422 | A1 * | 11/2008 | Ross | 604/408 |
| 2009/0036863 | A1 * | 2/2009 | Smith et al. | 604/408 |
| 2009/0037293 | A1 * | 2/2009 | Unger et al. | 705/27 |
| 2009/0206084 | A1 * | 8/2009 | Woolf et al. | 220/500 |
| 2009/0308391 | A1 * | 12/2009 | Smutney et al. | 128/203.15 |
| 2009/0308392 | A1 * | 12/2009 | Smutney et al. | 128/203.15 |
| 2010/0010471 | A1 * | 1/2010 | Ladd et al. | 604/514 |
| 2010/0021526 | A1 * | 1/2010 | Myers et al. | 424/443 |
| 2010/0052293 | A1 * | 3/2010 | Brooks et al. | 280/651 |

* cited by examiner

DRUG BAG CONTAINER

The present invention relates to a drug bag container.

BACKGROUND OF THE INVENTION

The drug industry employs bags made of flexible material, and each normally comprising an injection conduit and a feed conduit, which project from one edge of the bag to inject a drug into the bag, and to draw the drug from the bag respectively.

Bags of this sort are normally used on automatic drug manufacturing machines comprising a pocket store with a number of pockets, each for receiving and retaining a respective bag; a metering station for producing a drug inside each bag; and a grip-and-carry device for transferring the bags between the pocket store and the metering station.

To attach the bag to the pocket store and grip it using the grip-and-carry device, the bag is associated with a gripper comprising two contoured, substantially flat jaws, which are shorter in height than the injection and feed conduits, and are hinged to each other to rotate with respect to each other between a grip position gripping the injection and feed conduits, and a release position.

The gripper being designed to only grip the bag at one end, the bag is free to swing as it is being transferred by the grip-and-carry device. As a result, the bag is subject to shock and possible damage, the grip-and-carry device is forced to operate at a relatively slow travelling speed, and the bag takes a relatively long time to stabilize for operations such as weighing, thus resulting in relatively long operating cycles and relatively low output of known automatic machines of the type described.

SUMMARY OF THE INVENTION

It is an object of the present invention to provide a straightforward, low-cost drug bag container designed to eliminate the above drawbacks.

According to the present invention, there is provided a drug bag container as claimed in the accompanying Claims.

BRIEF DESCRIPTION OF THE DRAWINGS

A non-limiting embodiment of the present invention will be described by way of example with reference to the attached drawings, in which.

DETAILED DESCRIPTION OF THE INVENTION

Number 1 in the attached drawings indicates as a whole a container for a drug bag 2.

Bag 2 is made of flexible material, is substantially rectangular, and has two access conduits 3 and 4 projecting from an end edge 5. Conduit 3 is a feed conduit for drawing the drug from bag 2; and conduit 4 is an injection conduit for injecting the drug into bag 2.

Figure 2:
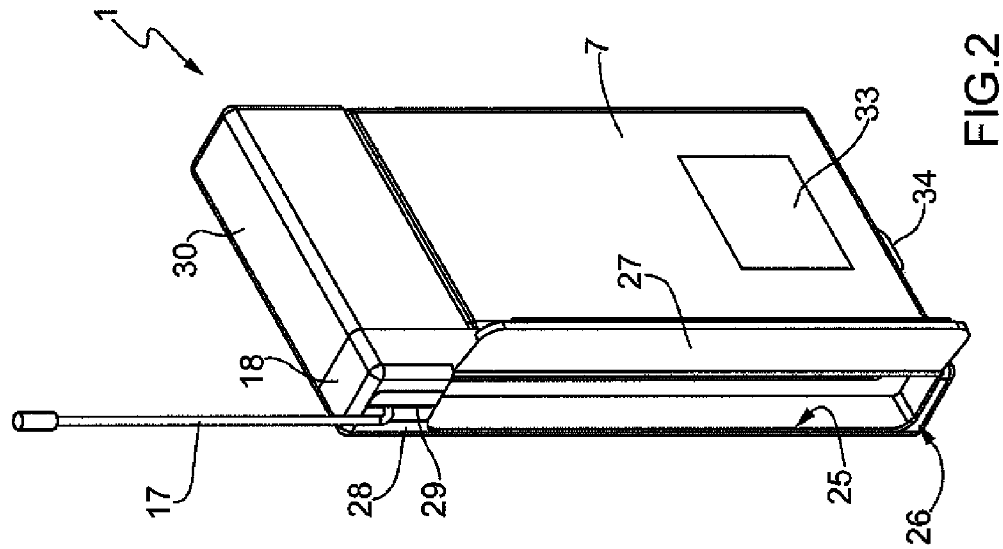
FIGS. 1 and 2 show views in perspective of a preferred embodiment of the container according to the present invention in two different operating positions.
Figure 1:
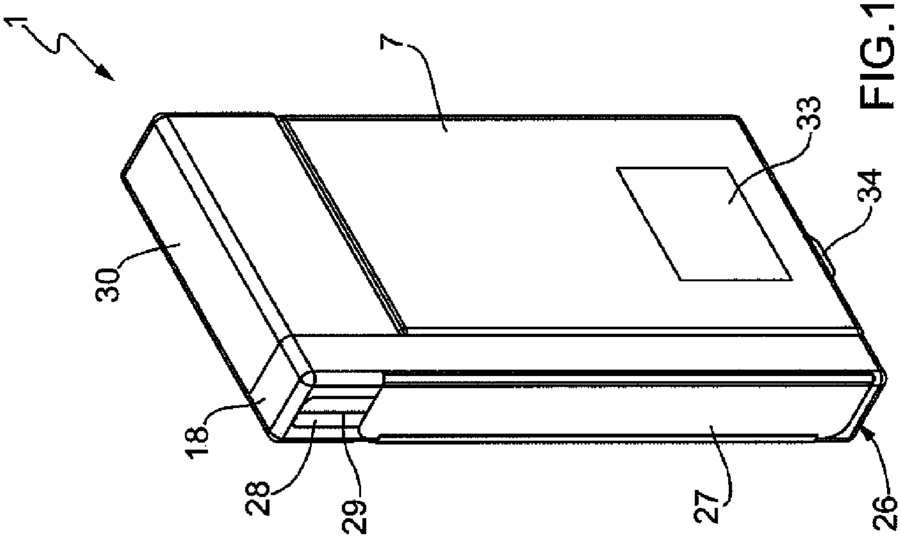
Figure 4:
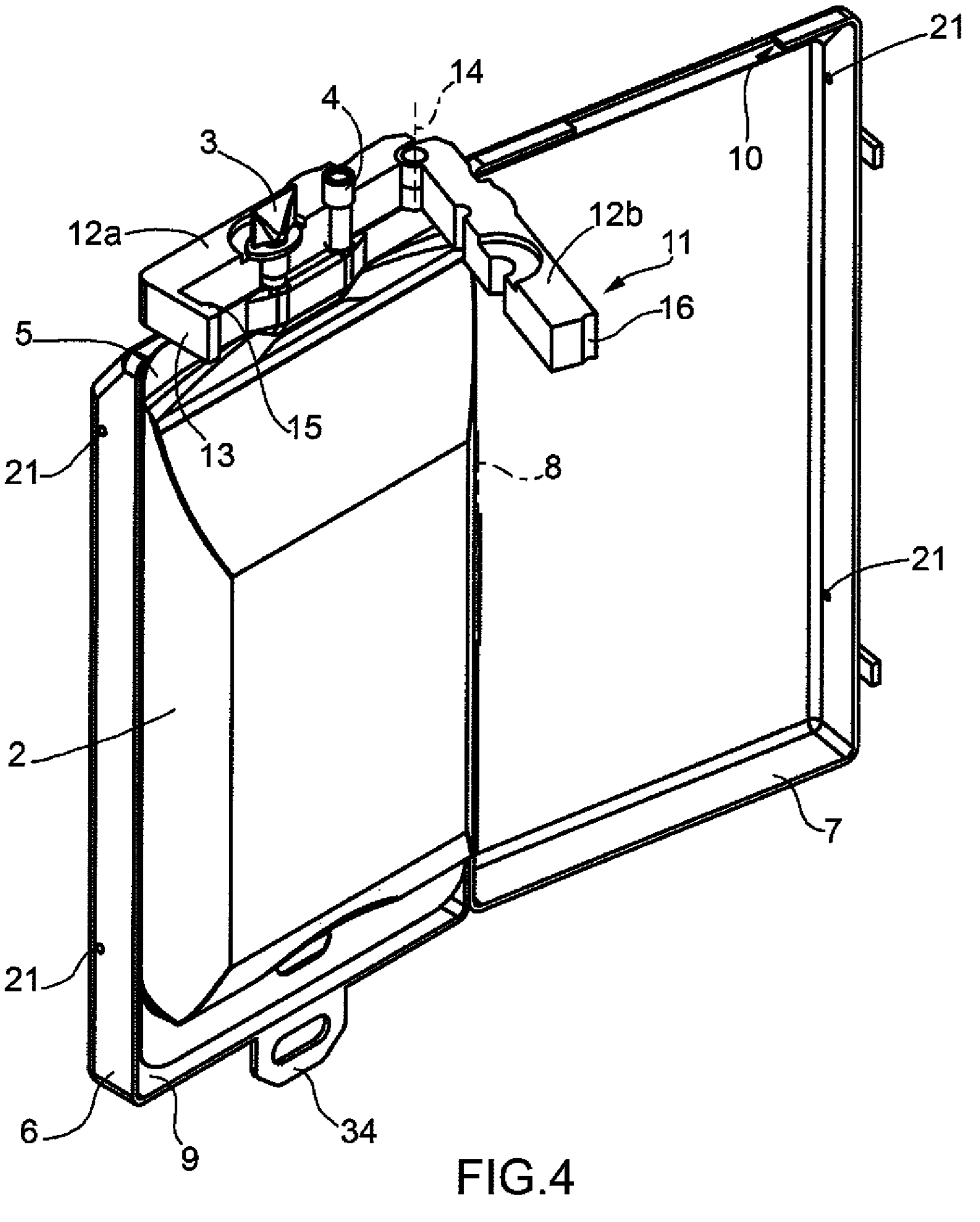
FIG. 4 shows a view in perspective of a detail in FIGS. 1 and 2.

Container 1 comprises two rigid shells 6 and 7 hinged to each other to rotate, with respect to each other and about a hinge axis 8, between an open position (FIG. 4), and a closed position (FIGS. 1 and 2) in which shells 6 and 7 define a compartment 9 for housing bag 2, and which has an opening 10 formed through shells 6 and 7 to allow conduits 3 and 4 to project outwards of compartment 9.

Container 1 also comprises a gripper 11 fitted outside shells 6 and 7, at opening 10, to allow a robot arm of an automatic drug manufacturing machine (not shown) to grip and retain bag 2.

Figure 3:
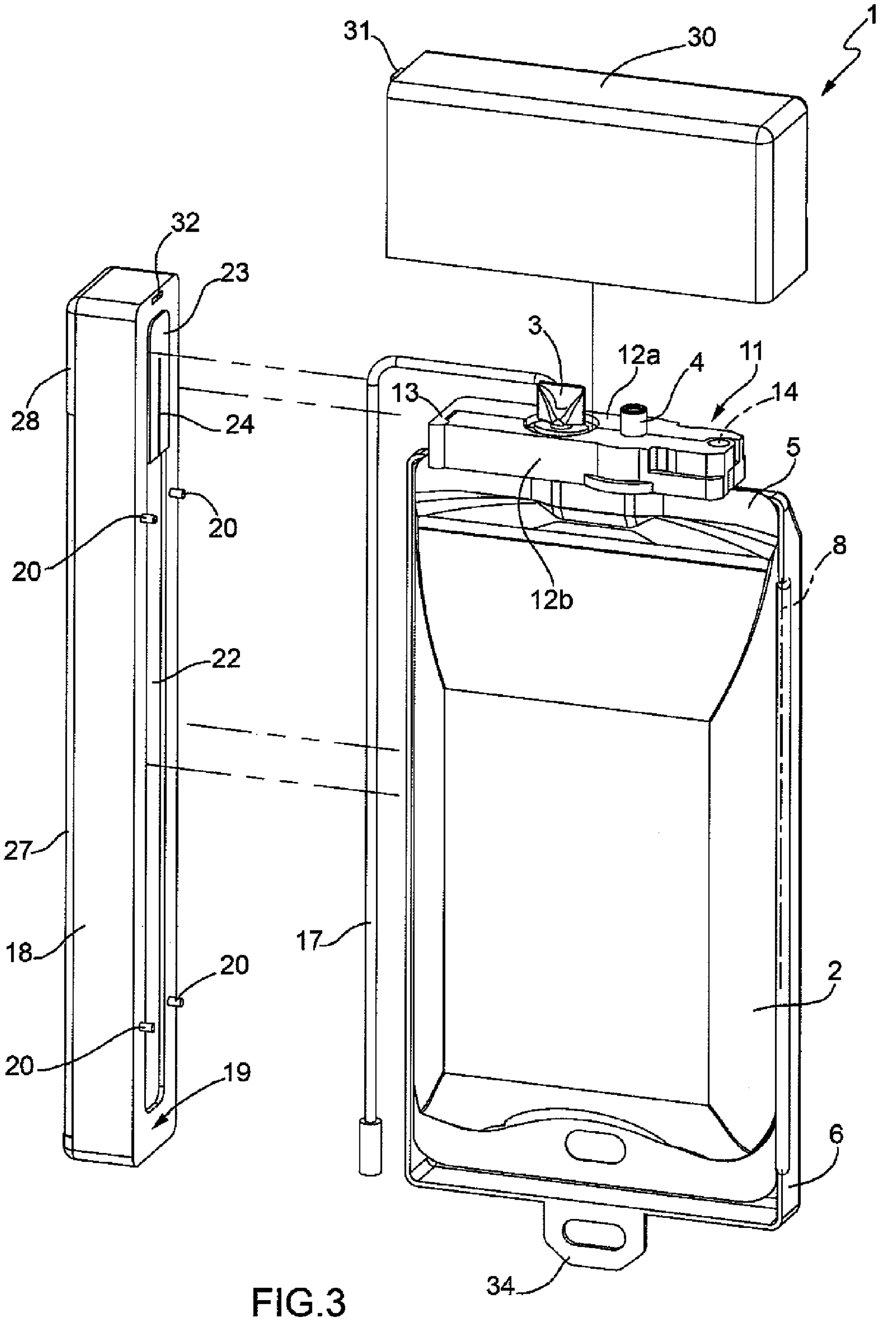
FIG. 3 shows an exploded view in perspective, with parts removed for clarity, of the FIGS. 1 and 2 container.

Gripper 11 comprises two flat, substantially rectangular jaws 12: one (hereinafter indicated 12*a*) is fixed to shell 6, is substantially L-shaped, and has an elastically deformable tab 13; and the other (hereinafter indicated 12*b*) is hinged to jaw 12*a* to rotate, with respect to jaw 12*a* and about a hinge axis 14 parallel to axis 8, between a grip position (FIG. 3) gripping conduits 3 and 4, and a release position (FIG. 4) releasing conduits 3 and 4.

Measured parallel to axis 8, jaws 12*a* and 12*b* are shorter in height than conduits 3 and 4, to allow conduits 3 and 4 to project outwards of gripper 11 when jaws 12*a* and 12*b* are in the grip position.

Jaws 12*a* and 12*b* are locked in the grip position by a tooth 15, formed on the free end of tab 13, engaging a recess 16 formed on the free end of jaw 12*b*.

Bag 2 also comprises a feed tube 17, which is connected to conduit 3, extends outside shells 6 and 7, extends substantially L-shaped about gripper 11 and a minor lateral face of each shell 6 and 7, and is protected by an elongated, substantially parallelepiped-shaped side cover 18.

Cover 18 is bounded by a flat face 19 positioned substantially contacting shells 6 and 7, and is fitted removably to shells 6 and 7 by a number of teeth 20, projecting crosswise to axis 8 from face 19, engaging corresponding cavities 21 formed through shells 6 and 7.

Cover 18 has a first opening 22 formed through face 19 to permit insertion of tube 17 inside cover 18, and which is partly closed by a rubber partition 23 with a slit 24 engaged by tube 17.

Cover 18 has a second opening 25, which is formed through a face 26, substantially opposite and parallel to face 19, of cover 18, and is closed partly by a door 27 for access to tube 17, and partly by a rubber partition 28 with a slit 29 engaged by tube 17.

Container 1 also comprises a substantially parallelepiped-shaped cover 30 fitted to shells 6 and 7, crosswise to cover 8, to cover conduits 3 and 4, gripper 11 and part of tube 17, and which is fixed removably to cover 18 by a tooth 31, projecting parallel to teeth 20 from cover 30, engaging a cavity 32 formed through face 19.

In actual use, once bag 2 is inserted between shells 6 and 7, shells 6 and 7 are closed; feed tube 17 is connected to feed conduit 3; and side cover 18 is fitted to shells 6 and 7 to cover tube 17.

At this point, the assembly formed by bag 2, shells 6 and 7, tube 17 and cover 18 is fed through said automatic machine (not shown) to inject at least one drug and/or at least one solvent into bag 2 to produce the drug.

Once the drug is produced, cover 30 is fitted onto shells 6 and 7 and fastened to cover 18 (FIG. 1), and container 1 is delivered to a hospital pharmacy.

To administer the drug, door 27 in cover 18 is opened, tube 17 is extracted from container 1 and bent through partition 28 (FIG. 2), door 27 is closed, and container 1 is hung from a known supporting rod (not shown) by a fastening device 34 on shell 6.

The invention claimed is:

1. A container for a drug bag, comprising:

two shells movable between a closed position, in which the two shells define a compartment for housing the drug bag, and an open position; and a gripper fitted outside of the compartment and comprising two jaws movable between a grip position and a release position to grip and release at least one access conduit allowing access to the content of the bag;

wherein a first jaw of the gripper is fixed to a first shell of the two shells, and a second jaw of the gripper is independently movable with respect to the first jaw of the gripper and a second shell of the two shells.

2. The container as claimed in claim 1, further comprising a first cover fitted removably to the two shells to cover the gripper and the access conduit.

3. The container as claimed in claim 1, wherein the drug bag comprises a feed tube connected to the access conduit outside of the two shells; and the container further comprising a second cover fitted removably to the two shells to cover the feed tube.

4. The container as claimed in claim 3, wherein the second cover comprises a door for access to the feed tube housed inside the second cover.

5. The container as claimed in claim 3, wherein the second cover is bounded by a first face positioned substantially contacting at least one of the two shells, the second cover comprises a first opening formed through the first face, and the second cover comprises a first rubber partition at least partly closing the first opening and comprising a first slit engaged by the feed tube.

6. The container as claimed in claim 3, wherein the second cover is bounded by a first face positioned substantially contacting at least one of the two shells, the second cover is bounded by a second face opposite the first face, the second cover comprises a second opening formed through the second face, and the second cover comprises a second rubber partition at least partly closing the second opening and comprising a second slit engaged by the feed tube.

7. The container as claimed in claim 1, further comprising a fastening device formed on the two shells by which to attach the container to a supporting rod.

* * * * *